(12) United States Patent
Minezaki et al.

(10) Patent No.: US 8,859,787 B2
(45) Date of Patent: Oct. 14, 2014

(54) GLYCOL COMPOUND HAVING DIOXANE STRUCTURE AND METHOD FOR PRODUCING THE SAME

(75) Inventors: Takuya Minezaki, Kanagawa (JP); Takeshi Hirokane, Kanagawa (JP); Dai Oguro, Kanagawa (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 659 days.

(21) Appl. No.: 13/143,677

(22) PCT Filed: Jan. 7, 2010

(86) PCT No.: PCT/JP2010/050107
§ 371 (c)(1),
(2), (4) Date: Jul. 7, 2011

(87) PCT Pub. No.: WO2010/079809
PCT Pub. Date: Jul. 15, 2010

(65) Prior Publication Data
US 2011/0269976 A1  Nov. 3, 2011

(30) Foreign Application Priority Data
Jan. 9, 2009  (JP) .................................. 2009-003659

(51) Int. Cl.
*C07D 319/06* (2006.01)
*G02B 1/04* (2006.01)

(52) U.S. Cl.
CPC .............. *C07D 319/06* (2013.01); *G02B 1/041* (2013.01)
USPC ....................................................... 549/374

(58) Field of Classification Search
CPC ............................... C07D 319/06; G02B 1/041
USPC ....................................................... 549/374
See application file for complete search history.

(56) References Cited

U.S. PATENT DOCUMENTS

| 5,350,822 | A  | 9/1994 | Chen |
| 2004/0146941 | A1 | 7/2004 | Zhang et al. |
| 2006/0251884 | A1 | 11/2006 | Naito et al. |

FOREIGN PATENT DOCUMENTS

| EP | 1 725 974 A2 | 11/2006 |
| EP | 1 725 974 A3 | 11/2006 |
| JP | 2002 128881 | 5/2002 |
| WO | 2004 041752 | 5/2004 |

OTHER PUBLICATIONS

U.S. Appl. No. 13/146,752, filed Jul. 28, 2011, Oguro.
Liu, Z. -I. et al., "Synthesis and Polymerization of Six-Membered Carbonate", J. Wuhan Uni. (Nat. Sci. Ed.), vol. 48, No. 6, pp. 645-648, (Dec. 2002).
El Ashry, E. S. H. et al., "Synthesis of Functionalised Derivatives of Pentaerythritol", J. Chem. Research (S), J. Chem. Research (M), pp. 2-3 (S), pp. 0111-0128 (M), (2003).
International Search Report issued Mar. 30, 2010 in PCT/JP10/050107 filed Jan. 7, 2010.
U.S. Appl. No. 13/143,612, filed Jul. 7, 2011, Minezaki, et al.
Extended Supplementary European Search Report issued on Mar. 29, 2012 in corresponding European Application No. 10 72 9229.

*Primary Examiner* — T. Victor Oh
(74) *Attorney, Agent, or Firm* — Oblon, Spivak, McClelland, Maier & Neustadt, L.L.P.

(57) ABSTRACT

Disclosed is a glycol compound which is useful as a raw material and an intermediate for synthetic resins, additives for synthetic resins, medicines, cosmetics, food additives, surfactants and the like, further disclosed is a method for producing the compound.

The glycol compound is represented by the following Formula (1):

(1)

$(R)_n$—[phenyl]—CH(O—CH$_2$)$_2$C(CH$_2$OH)$_2$ wherein R represents an alkyl group having 1 to 12 carbon atoms, a substituted or unsubstituted aryl group having 6 to 10 carbon atoms or a halogen atom; n represents an integer of 1 to 4; and when n represents an integer of 2 to 4, plural R may be the same or different from each other.

16 Claims, No Drawings

GLYCOL COMPOUND HAVING DIOXANE STRUCTURE AND METHOD FOR PRODUCING THE SAME

This application is a 371 of PCT/JP2010/050107, filed Jan. 7, 2010. Priority to Japanese patent application 2009-003659, filed Jan. 9, 2009, is claimed.

TECHNICAL FIELD

The present invention relates to a glycol compound having a dioxane structure and a method for producing the same, particularly to a glycol compound useful as a raw material and an intermediate for synthetic resins, additives for synthetic resins, medicines, cosmetics, food additives, surfactants and the like and a method for producing the above compound.

BACKGROUND ART

Glycol compounds having a dioxane structure are known as intermediates for combinatorial synthesis for drug discovery. Patent document 1 disclosed glycol compounds obtained by condensation of p-anisaldehyde and pentaerythritol, as intermediates of base materials (tag) used for combinatorial synthesis. Glycol compounds having a dioxane structure are excellent in an adhesive property with the respective resins, a weatherability, a suited heat resistance and the like, and therefore they are useful as raw materials for various synthetic resins and the like (refer to, for example, Patent document 2).

CITATION LIST

Patent Literature

[Patent document 1] U.S. Patent Publication No. 2004/146941
[Patent document 2] JP-A-2002-128881

SUMMARY OF INVENTION

Technical Problem

The glycol compounds obtained by condensation of p-anisaldehyde and pentaerythritol, which are described in the Patent document 1, are limited in uses thereof in a certain case in terms of a solubility, a reactivity, a heat resistance and the like as far as use thereof for combinatorial synthesis is concerned.

The present invention contemplates to provide a glycol compound useful as a raw material and an intermediate for synthetic resins, additives for synthetic resins, medicines, cosmetics, food additives, surfactants and the like and a method for producing the above compound.

Solution to Problem

The present invention provides a glycol compound represented by the following Formula (1):

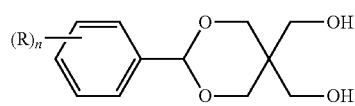

wherein R represents an alkyl group having 1 to 12 carbon atoms, a substituted or unsubstituted aryl group having 6 to 10 carbon atoms or a halogen atom; n represents an integer of 1 to 4; and when n represents an integer of 2 to 4, plural R may be the same or different from each other.

Advantageous Effects of Invention

The glycol compound of the present invention can suitably be used as a raw material and an intermediate for synthetic resins, additives for synthetic resins, medicines, cosmetics, food additives, surfactants and the like. In particular, a polyester resin which is excellent in a moldability and a heat resistance and which has a low Abbe number and a high refractive index can be obtained by using the glycol compound of the present invention as a raw material for the polyester resin. Further, medicines, cosmetics, food additives, surfactants and the like which are rich in variety can be produced by using the glycol compound of the present invention as a raw material and an intermediate therefor.

DESCRIPTION OF EMBODIMENTS

The glycol compound of the present invention is a compound represented by the following Formula (1):

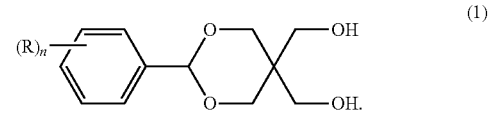

In Formula (1) described above, R represents an alkyl group having 1 to 12 carbon atoms, a substituted or unsubstituted aryl group having 6 to 10 carbon atoms or a halogen atom.

The alkyl group in the present invention is a linear, branched or cyclic alkyl group having 1 to 12 carbon atoms, preferably 1 to 9 carbon atoms, more preferably 1 to 4 carbon atoms, and the specific examples thereof include methyl, ethyl, propyl, isopropyl, butyl, isobutyl, t-butyl, cyclohexyl, propylcyclohexyl and the like. The aryl group in the present invention is a substituted or unsubstituted aryl group having 6 to 10 carbon atoms, preferably 6 to 8 carbon atoms, and the specific examples thereof include phenyl, iodophenyl, dihydroxyphenyl, methoxyhydroxyphenyl, ethoxyhydroxyphenyl and the like. The halogen atom includes a fluorine atom, a chlorine atom, a bromine atom and an iodine atom. R is particularly preferably isopropyl or phenyl from the viewpoint of an availability of the raw materials.

In Formula (1) described above, n represents an integer of 1 to 4, and when n represents an integer of 2 to 4, plural R may be the same or different from each other, but they are more preferably the same. The term n is preferably 1 from the viewpoint of an availability of the raw materials.

The glycol compound represented by Formula (1) described above is preferably a glycol compound represented by the following Formula (2), that is, 2-(biphenyl-4-yl)-5,5-di(hydroxymethyl)-1,3-dioxane. Also, it is preferably a glycol compound represented by the following Formula (3), that is, 2-(isopropylphenyl-4-yl)-5,5-di(hydroxymethyl)-1,3-dioxane.

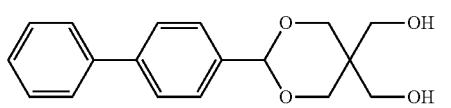 [SMILES: OCC1(CO)COC(c2ccc(-c3ccccc3)cc2)OC1]

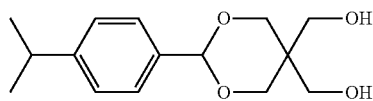

A method for producing the glycol compound represented by Formula (1) described above shall not specifically be restricted, and a method for producing it by reacting 1 mol of aromatic aldehyde represented by the following Formula (A) with 1 to 5 mol of pentaerythritol is preferred.

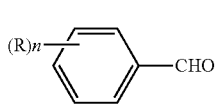

wherein R and n are the same as R and n in Formula (1) described above.

If dehydration reaction is carried out in a proportion of less than 1 mol of pentaerythritol based on 1 mol of the aromatic aldehyde represented by Formula (A), a compound represented by the following Formula (4) is formed as a by-product. The above by-product is a compound obtained by condensing 1 mol of pentaerythritol with 2 mol of the aromatic aldehyde represented by Formula (A) described above. When the glycol compound of the present invention is used for various resins and the like, the above by-product exerts an influence on the various physical properties thereof in a certain case, and therefore the by-product is preferably reduced.

wherein R and n are the same as R and n in Formula (A) described above.

In the method for producing the glycol compound of the present invention, reacting 1 mol of the aromatic aldehyde represented by Formula (A) described above with 1 to 5 mol, preferably 1.05 to 5 mol, and more preferably 1.3 to 2 mol of pentaerythritol makes it possible to reduce notably formation of the compound represented by Formula (4) described above and to enhance the production efficiency.

In the method for producing the glycol compound of the present invention, the reaction temperature is preferably 20 to 200° C., more preferably 100 to 180° C., and particularly preferably 120 to 160° C. The targeted compound can efficiently be produced by manufacturing the compound at temperatures falling in the ranges described above.

In the method for producing the glycol compound of the present invention, the aromatic aldehyde described above is preferably dropwise added to an organic solvent solution of pentaerythritol under the presence of an acid catalyst to react them. This makes it possible to reduce notably formation of the compound represented by Formula (4) described above and to enhance the production efficiency. Further, during the reaction, water contained in the solvent is preferably removed by distillation under the presence of the acid catalyst.

Acid catalysts such as hydrochloric acid, sulfuric acid, phosphoric acid, paratoluenesulfonic acid, methanesulfonic acid and the like are preferably used as the catalyst which can be used in the present invention, and paratoluenesulfonic acid is particularly preferred. Also, an amount of the acid catalyst used is preferably 0.1 to 30% by mass, particularly preferably 1 to 20% by mass based on the aromatic aldehyde.

The reaction solvent used in the present invention shall not be restricted and is preferably aromatic hydrocarbon base solvents such as benzene, toluene, xylene, mesitylene, anisole and the like; amide base solvents such as dimethylformamide, dimethylacetamide and the like; ether base solvents such as tetrahydrofuran, dioxane, dioxolan and the like; and ester base solvents such as ethyl acetate, butyl acetate and the like. In particular, toluene, dimethylformamide and dimethylacetamide are preferred.

The glycol compound of the present invention can be used as a raw material for polyester resins. For example, polyester resins which contain diol units originating in ethylene glycol and the glycol compound represented by Formula (1) described above and an aromatic dicarboxylic acid unit, and which comprise a unit originating in ethylene glycol in a proportion of 40 to 99 mol % based on the whole diol units and a unit originating in the glycol compound represented by Formula (1) in a proportion of 1 to 60 mol % based on the whole diol units can be produced by using the glycol compound of the present invention. The above polyester resins are low in a crystallinity and excellent in a moldability and have a low Abbe number and a high refractive index. The above polyester resins can be injection-molded and can provide a molded article which is not whitened in molding and is transparent. Also, they have a low Abbe number and a high refractive index and therefore can suitably be used as a material of a lens for correcting aberration.

EXAMPLES

The present invention shall be explained below in detail with reference to examples, but the present invention shall not be restricted to the examples shown below.

Example 1

Synthesis of 2-(biphenyl-4-yl)-5,5-di(hydroxymethyl)-1,3-dioxane (Hereinafter Referred to as MPBP)

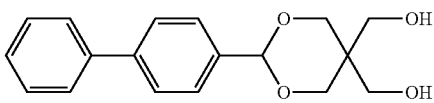

A 5,000 ml flask was charged with 2,000 ml of dimethylacetamide (hereinafter referred to as DMAc, special grade, manufactured by Wako Pure Chemical Industries, Ltd.), 700 ml of toluene (special grade, manufactured by Wako Pure Chemical Industries, Ltd.), 200 g (1.47 mol) of pentaerythritol (special grade, manufactured by Wako Pure Chemical Industries, Ltd.) and 20 g of paratoluenesulfonic acid dihydrate (special grade, manufactured by Wako Pure Chemical Industries, Ltd.), and the mixture was stirred at 100° C. Then, 700 ml of a toluene solution including 134 g (0.74 mol) of 4-biphenylaldehyde (special grade, manufactured by Wako Pure Chemical Industries, Ltd.) was dropwise added thereto and heated up to 145° C. A distillate containing water was separated, and the reaction was finished in a reaction time of 5 hours. 5 L of water was put into the reaction liquid, and white crystals were deposited. They were filtrated, washed with water and then concentrated to thereby obtain white crystals (yield: 98%).

The product obtained above was subjected to measurement of a $^1$H-NMR spectrum. An NMR equipment (trade name: R-90H, manufactured by Hitachi, Ltd.) was used for the measurement, and tetramethylsilane (hereinafter referred to as TMS; special grade, manufactured by Wako Pure Chemical Industries, Ltd.) was used as an internal standard substance. The chemical shift values (δ ppm, based on TMS) of $^1$H-NMR of the product obtained in a deuterated dimethylsulfoxide (hereinafter referred to as deuterated DMSO; special grade, manufactured by Wako Pure Chemical Industries, Ltd.) solvent were 3.2-3.4 (d, 4H), 3.6-4.1 (m, 4H), 4.4-4.7 (q, 2H), 5.5 (s, 1H), 7.3-7.8 (m, 9H), and the above product was identified as MPBP.

Example 2

Synthesis of 2-(isopropylphenyl-4-yl)-5,5-di(hydroxymethyl)-1,3-dioxane

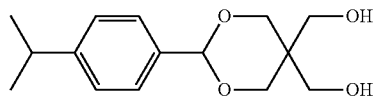 [SMILES: CC(C)c1ccc(C2OCC(CO)(CO)CO2)cc1]

Synthesis and analysis were carried out in the same manners as in Example 1, except that 4-biphenylaldehyde was changed to cumylaldehyde. The yield was 98%. The chemical shift values (δ ppm, based on TMS) of $^1$H-NMR of the product obtained in the deuterated DMSO solvent were 1.2 (d, 6H), 2.9-3.0 (m, 1H), 3.4-3.5 (s, 4H), 3.6-3.8 (dd, 4H), 4.7 (s, 2H), 5.9 (s, 1H), 7.2-7.5 (m, 4H).

Example 3

Synthesis of 2-(cyclohexylphenyl-4-yl)-5,5-di(hydroxymethyl)-1,3-dioxane

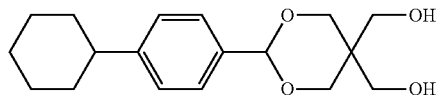 [SMILES: OCC1(CO)COC(c2ccc(C3CCCCC3)cc2)OC1]

Synthesis and analysis were carried out in the same manners as in Example 1, except that 4-biphenylaldehyde was changed to 4-cyclohexylbenzaldehyde. The yield was 89%. The chemical shift values (δ ppm, based on TMS) of $^1$H-NMR of the product obtained in the deuterated DMSO solvent were 1.3-1.9 (m, 10H), 2.7-2.8 (m, 1H), 3.4-3.5 (s, 4H), 3.6-3.8 (dd, 4H), 4.7 (s, 2H), 5.9 (s, 1H), 7.2-7.5 (m, 4H).

Example 4

Synthesis of 2-(biphenyl-4-yl)-5,5-di(hydroxymethyl)-1,3-dioxane (Another Method)

Synthesis and analysis were carried out in the same manners as in Example 1, except that an addition amount of pentaerythritol was changed to 100 g (0.74 mol). As a result thereof, white crystals (yield: 83%) were obtained. It was identified from chemical shift values of $^1$H-NMR that the compound obtained in the present example was the same compound as the compound obtained in Example 1.

Example 5

Synthesis of 2-(biphenyl-4-yl)-5,5-di(hydroxymethyl)-1,3-dioxane (Another Method) (Collective Charge Method)

A 5,000 ml flask was charged with 2,000 ml of DMAc, 1,400 ml of toluene, 200 g (1.47 mol) of pentaerythritol, 134 g (0.74 mol) of biphenylaldehyde and 20 g of paratoluenesulfonic acid dihydrate, and the mixture was stirred at 100° C. Then, it heated up to 145° C. A distillate containing water was separated, and the reaction was finished in a reaction time of 5 hours. 5 L of water was put into the reaction liquid, and white crystals were deposited. They were filtrated, washed with water and then concentrated to thereby obtain white crystals (yield: 90%). It was identified from chemical shift values of $^1$H-NMR that the compound obtained in the present example was the same compound as the compound obtained in Example 1.

Example 6

Production of Polyester Resin

The glycol compound (MPBP) obtained in Example 1 was used to produce a polyester resin.

A glass-made flask equipped with a heating device, a stirring blade, a partial condenser, a trap, a thermometer and a nitrogen gas introducing tube was charged with raw material monomers of kinds and amounts shown in Table 1, and the temperature was elevated up to 215° C. under the presence of 0.03 mol % of manganese acetate tetrahydrate based on the dicarboxylic acid component under nitrogen atmosphere to carry out transesterification. After a reaction conversion rate of the dicarboxylic acid component reached 90% or more, 0.02 mol % of antimony (III) oxide and 0.06 mol % of triethyl phosphate based on 100 mol % of the dicarboxylic acid component were added thereto, and temperature elevation and pressure reduction were gradually carried out. Finally, polycondensation was carried out at 250 to 270° C. and 0.1 kPa or less. The reaction was finished when the suited melt viscosity was obtained, and the polyester resin was recovered.

Comparative Examples 1 and 2

Production of Polyester Resins

A polyester manufacturing apparatus equipped with a filling column type fractionating tower, a partial condenser, a full condenser, a cold trap, a stirring device, a heating device and a nitrogen introducing tube was charged with raw material monomers of kinds and amounts shown in Table 1, and the temperature was elevated up to 215° C. under the presence of 0.03 mol % of manganese acetate tetrahydrate based on the dicarboxylic acid component under nitrogen atmosphere to carry out transesterification. After a reaction conversion rate of the dicarboxylic acid component reached 90% or more, 0.02 mol % of antimony (III) oxide and 0.06 mol % of triethyl phosphate based on 100 mol % of the dicarboxylic acid component were added thereto, and temperature elevation and pressure reduction were gradually carried out. Finally, polycondensation was carried out at 250 to 270° C. and 0.1 kPa or less. The reaction was finished when the suited melt viscosity was obtained, and the polyester resin was recovered.

TABLE 1

|  |  | Example | Comparative Example | |
|---|---|---|---|---|
|  |  | 6 | 1 | 2 |
| Dicarboxylic acid component (mol) | Dimethyl 2,6-naphthalene dicarboxylate | 0.940 | 218.5 | 0 |
|  | Dimethyl terephthalate | 0 | 0 | 369.5 |
| Diol component (mol) | MPBP | 0.094 | 0 | 0 |
|  | Ethylene glycol | 1.597 | 393.3 | 591.2 |

MPBP: 2-(biphenyl-4-yl)-5,5-di(hydroxymethyl)-1,3-dioxane (Production of Optical Lens)

The polyester resins obtained in Example 6 and Comparative Examples 1 and 2 were subjected to vacuum drying at a temperature which was lower by 20° C. than a glass transition temperature of the resin for 10 hours, and then they were subjected to injection molding by means of an injection molding equipment (trade name: SH50, manufactured by Sumitomo Heavy Industries, Ltd.) at a cylinder temperature of 260° C. and a metal die temperature which was set to a temperature lower by 35° C. than a glass transition temperature of the resin, whereby biconvex lenses having a diameter of 28 mm and a curvature radius of 20 mm in both convex faces were obtained.

The compositions and the physical properties of the polyester resins obtained in Example 6 and Comparative Examples 1 and 2 were measured by the following methods. Also, the lenses obtained in Example 6 and Comparative Examples 1 and 2 were evaluated by the following methods. The results thereof are shown in Table 2.

<Measuring Methods for Compositions and Physical Properties of the Polyester Resins>

(1) Resin Composition:

A proportion of the diol unit and the dicarboxylic acid unit in the polyester resin was calculated by $^1$H-NMR measurement. It was measured by means of an NMR apparatus (trade name: JNM-AL400, manufactured by JEOL Ltd.) at 400 MHz. Deuterated chloroform was used for the solvent.

(2) Glass Transition Temperature (Tg):

A glass transition temperature of the polyester resin was measured by means of a differential scanning colorimeter (trade name: DSC/TA-60WS, manufactured by Shimadzu Corporation). A non-sealed vessel made of aluminum was charged with about 10 mg of the polyester resin and heated up to 280° C. at a heating rate of 20° C./minute under nitrogen gas flow (30 ml/minute) to melt the resin, and it was quenched to prepare a sample for measurement. The above sample was measured on the above conditions to calculate the middle point glass transition temperature based on JIS Standard K7121.

(3) Intrinsic Viscosity (IV):

An intrinsic viscosity of the polyester resin was measured at 25° C. by means of a capillary viscometer automatic measuring device (trade name: SS-300-L1, manufactured by Shibayama Scientific Co., Ltd.). The polyester resin 0.5 g was dissolved in 120 g of a mixed solvent (mass ratio=6:4) of phenol/1,1,2,2-tetrachloroethane by heating, and the solution was filtrated and then cooled down to 25° C. to prepare a sample for measurement.

(4) Refractive Index and Abbe Number:

A refractive index and an Abbe number of the polyester resin were measured at 25° C. by means of an Abbe viscometer (trade name: NAR-4T, manufactured by Atago Co., Ltd.). The polyester resin was subjected to vacuum drying at a temperature lower by about 20° C. than a glass transition temperature of the resin for 10 hours, and then it was subjected to injection molding by means of the injection molding equipment (trade name: SH50, manufactured by Sumitomo Heavy Industries, Ltd.) at a cylinder temperature of 280° C. and a metal die temperature which was set to a temperature lower by 20 to 50° C. than a glass transition temperature of the resin, and it was molded into an isosceles right triangle (3 mm thick) in which a length of two sides interposing the right angle therebetween was 20 mm respectively. The above molded piece was subjected to annealing treatment for 10 hours in an oven of a temperature lower by about 20° C. than a glass transition temperature of the resin to prepare a sample for measurement. The refractive index was measured at 589 nm (d-line). The Abbe number was calculated from the refractive indexes measured at 656 nm (C-line), 486 nm (F-line) and the d-line.

(5) Melt Mass Flow Rate (MFR):

A melt mass flow rate of the polyester resin was measured by means of a melt indexer (trade name: C-5059D, manufactured by Toyo Seiki Seisakusho, Ltd.). It was measured on the conditions of a measuring temperature of 260° C. and a load of 2.16 kgf based on JIS Standard K7210.

<Evaluating Method for Optical Lens>

(6) Appearance Evaluation:

An appearance of the optical lens was visually observed to evaluate a transparency and the presence of deformation such as sinks, cambers and the like.

TABLE 2

|  |  | Example | Comparative Example | |
|---|---|---|---|---|
|  |  | 6 | 1 | 2 |
| Composition and physical properties of polyester resin | | | | |
| Copolymerization composition (mol %) | Dimethyl 2,6-naphthalene-dicarboxylate | 100 | 100 | 0 |
|  | Dimethyl terephthalate | 0 | 0 | 100 |
|  | MPBP | 10 | 0 | 0 |
|  | Ethylene glycol | 90 | 100 | 100 |
| Glass transition temperature (° C.) | | 115 | 124 | 84 |
| Intrinsic viscosity (dl/g) | | 0.28 | 0.55 | 0.72 |
| Refractive index | | 1.646 | 1.649 | 1.575 |
| Abbe number | | 18.7 | 65 | 39 |
| MFR (g/10 minutes) | | 178 | 4.8 | 5.3 |
| Evaluation of optical lens | | | | |
| Transparency | | Good | Whitened | Whitened |
| Presence of deformation | | None | Present | Present |

MPBP: 2-(biphenyl-4-yl)-5,5-di(hydroxymethyl)-1,3-dioxane

The polyester resin in Example 6 which was produced by using the glycol compound obtained in Example 1 had a low intrinsic viscosity and a high melt mass flow rate and was excellent in an injection moldability, and it had a low Abbe number and a high refractive index as compared with the polyester resins (PEN and PET) produced in Comparative Examples 1 and 2. The optical lens obtained by subjecting the polyester resin obtained in Example 6 to injection molding was excellent in a transparency and did not cause deformation by sinks and cambers as compared with those obtained by using the polyester resins produced in Comparative Examples 1 and 2, and in addition thereto, it had a low Abbe number and a high refractive index. Accordingly, it is excellent as a lens for correcting aberration.

Further, a glass transition temperature of the polyester resin prepared in Example 6 is a little lower than that of PEN alone (Comparative Example 1) but sufficiently higher than that of PET alone (Comparative Example 2). Usually, when a crystallinity of PET and PEN is tried to be improved, a glass transition temperature thereof is reduced, and therefore a heat resistance thereof is reduced. In contrast with this, use of the glycol compound of the present invention makes it possible to obtain the polyester resin having a glass transition temperature which is not lower than that of PET alone and which is almost equivalent to that of PEN while maintaining sufficiently a low crystallinity and a moldability as a molding material.

Further, polyester resins and optical lenses were produced in the same manners as described above, except that in Example 6, the glycol compound prepared in Example 1 was changed to the glycol compound prepared in Example 2 or 3, and they showed excellent properties as was the case with the polyester resin and the optical lens produced in Example 6.

[Industrial Applicability]

The glycol compound of the present invention can suitably be used as a raw material and an intermediate for synthetic resins, additives for synthetic resins, medicines, cosmetics, food additives, surfactants and the like, and it has a high industrial value. In particular, a polyester resin which is excellent in a moldability and which has a low Abbe number and a high refractive index can be obtained by using the glycol compound of the present invention as a raw material for a polyester resin. The above polyester resin can suitably be used as a material of a lens for correcting aberration. Even when conventional glycol compounds can not be used as raw materials or intermediates in combinatorial synthesis, the glycol compound of the present invention can be used as a raw material or an intermediate therefor to make it possible to produce various medicines, cosmetics, food additives, surfactants and the like, and the technique can be enriched.

The invention claimed is:

1. A compound represented by Formula (2):

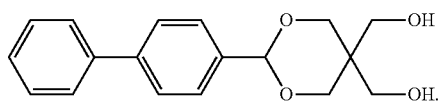
(2)

2. A method for producing a compound represented by Formula (2):

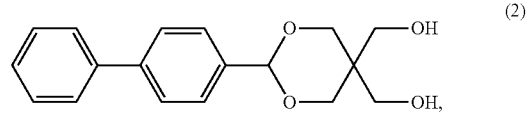
(2)

said method comprising reacting 1 mol of 4-biphenylaldehyde with 1 to 5 mol of pentaerythritol.

3. The method according to claim 2, wherein the 4-biphenylaldehyde is dropwise added to an organic solvent solution comprising pentaerythritol and an acid catalyst.

4. The method of claim 3, wherein said acid catalyst comprises an acid selected from the group consisting of hydrochloric acid, sulfuric acid, phosphoric acid, paratoluenesulfonic acid, and methanesulfonic acid.

5. The method of claim 3, wherein said organic solvent solution comprises an organic solvent selected from the group consisting of benzene, toluene, xylene, mesitylene, anisole, dimethylformamide, dimethylacetamide, tetrahydrofuran, dioxane, dioxolan, ethyl acetate, and butyl acetate.

6. The method of claim 3, wherein said acid catalyst is paratoluenesulfonic acid, and wherein said organic solvent solution comprises an organic solvent selected from the group consisting of toluene, dimethylformamide and dimethylacetamide.

7. The method according to claim 2, comprising reacting 1 mol of 4-biphenylaldehyde with 1.05 to 5 mol of pentaerythritol.

8. The method according to claim 2, comprising reacting 1 mol of 4-biphenylaldehyde with 1.3 to 2 mol of pentaerythritol.

9. The method according to claim 3, comprising reacting 1 mol of 4-biphenylaldehyde with 1.05 to 5 mol of pentaerythritol.

10. The method according to claim 3, comprising reacting 1 mol of 4-biphenylaldehyde with 1.3 to 2 mol of pentaerythritol.

11. The method according to claim 4, comprising reacting 1 mol of 4-biphenylaldehyde with 1.05 to 5 mol of pentaerythritol.

12. The method according to claim 4, comprising reacting 1 mol of 4-biphenylaldehyde with 1.3 to 2 mol of pentaerythritol.

13. The method according to claim 5, comprising reacting 1 mol of 4-biphenylaldehyde with 1.05 to 5 mol of pentaerythritol.

14. The method according to claim 5, comprising reacting 1 mol of 4-biphenylaldehyde with 1.3 to 2 mol of pentaerythritol.

15. The method according to claim 6, comprising reacting 1 mol of 4-biphenylaldehyde with 1.05 to 5 mol of pentaerythritol.

16. The method according to claim 6, comprising reacting 1 mol of 4-biphenylaldehyde with 1.3 to 2 mol of pentaerythritol.

* * * * *